United States Patent
Nagaike et al.

(10) Patent No.: US 12,414,925 B2
(45) Date of Patent: Sep. 16, 2025

(54) EXTERNAL COMPOSITION

(71) Applicant: Kobayashi Pharmaceutical Co., Ltd., Osaka (JP)

(72) Inventors: Daisaku Nagaike, Dalton, GA (US); Tsuyoshi Igaue, Dalton, GA (US)

(73) Assignee: Kobayashi Pharmaceutical Co., Ltd., Osaka (JP)

( * ) Notice: Subject to any disclaimer, the term of this patent is extended or adjusted under 35 U.S.C. 154(b) by 976 days.

(21) Appl. No.: 17/418,418

(22) PCT Filed: Dec. 26, 2019

(86) PCT No.: PCT/IB2019/061381
§ 371 (c)(1),
(2) Date: Jun. 25, 2021

(87) PCT Pub. No.: WO2020/136607
PCT Pub. Date: Jul. 2, 2020

(65) Prior Publication Data
US 2022/0047533 A1    Feb. 17, 2022

Related U.S. Application Data

(60) Provisional application No. 62/785,358, filed on Dec. 27, 2018.

(51) Int. Cl.
| | | |
|---|---|---|
| *A61K 31/167* | (2006.01) | |
| *A61K 9/00* | (2006.01) | |
| *A61K 9/06* | (2006.01) | |
| *A61K 9/70* | (2006.01) | |
| *A61K 47/10* | (2017.01) | |
| *A61K 47/32* | (2006.01) | |

(52) U.S. Cl.
CPC .......... *A61K 31/167* (2013.01); *A61K 9/0014* (2013.01); *A61K 9/06* (2013.01); *A61K 9/7007* (2013.01); *A61K 47/10* (2013.01); *A61K 47/32* (2013.01)

(58) Field of Classification Search
CPC ...... A61K 47/10; A61K 47/32; A61K 31/167; A61K 9/0014; A61K 9/06; A61K 9/7007; A61K 9/70
See application file for complete search history.

(56) References Cited

U.S. PATENT DOCUMENTS

| | | | |
|---|---|---|---|
| 6,328,982 B1 * | 12/2001 | Shiroyama | A61Q 19/00 568/300 |
| 10,307,380 B1 | 6/2019 | Mantelle | |
| 2017/0087199 A1 | 3/2017 | Patron et al. | |
| 2018/0057447 A1 | 3/2018 | Itoh et al. | |

FOREIGN PATENT DOCUMENTS

| | | | | |
|---|---|---|---|---|
| EP | 0988852 A2 | | 3/2000 | |
| EP | 1197205 A2 | | 4/2002 | |
| JP | H1072312 | * | 3/1998 | |
| JP | 2004210668 A | * | 7/2004 | |
| JP | 2013-136532 A | | 7/2013 | |
| JP | 2014-152172 A | | 8/2014 | |
| JP | 2018083069 A | * | 5/2018 | ............. B23D 17/00 |
| WO | 2016/153011 A1 | | 9/2016 | |

OTHER PUBLICATIONS

JPH1072312, text (Year: 2024).*
JP2018-083069 (Year 2018).*
International Search Report issued in corresponding International Patent Application No. PCT/IB2019/061381 dated Mar. 31, 2020.
Written Opinion issued in corresponding International Patent Application No. PCT/IB2019/061381 dated Mar. 31, 2020.

* cited by examiner

*Primary Examiner* — Snigdha Maewall
(74) *Attorney, Agent, or Firm* — Morgan, Lewis & Bockius LLP

(57) ABSTRACT

The present disclosure provides an external composition containing lidocaine, a cool feeling agent, and vanillyl butyl ether.

17 Claims, No Drawings

EXTERNAL COMPOSITION

TECHNICAL FIELD

The present disclosure relates to an external composition containing lidocaine and a cool feeling agent. More specifically, the present disclosure relates to an external composition whose cooling effect maintains for a long time. The present disclosure also relates to a patch using the external composition.

BACKGROUND ART

A cool feeling agent such as menthol is usually compounded in an external composition for the purpose of cooling the affected part and giving refreshing feeling. However, in some cases, the cool feeling effect is not sufficient and is not maintained for a long duration. In particular, when a local anesthetic is compounded, there is a problem in that cooling effect is less likely to be felt due to the anesthetic effect. Such a difficulty in sensing a cool feeling is not improved even when only a cool feeling agent is compounded.

In view of such conventional art, development of an external composition and a patch with a cool feeling maintained for a long duration even when a local anesthetic such as lidocaine is compounded is much required.

CITATION LIST

Patent Literature

[Patent Literature 1] U.S. Patent No. 2017/0087199A1
[Patent Literature 2] International Publication No. WO2016/153011

SUMMARY OF INVENTION

Technical Problem

One object of some embodiments described herein is to provide an external composition which maintains a cool feeling effect for a long time even when lidocaine is compounded therein. Another object of some embodiments is to provide a patch using the external composition.

Solution to Problem

In addition to a cool feeling agent, a warm feeling agent such as nonanoic acid vanillyl amide, capsaicin or chili peppers is compounded in an external preparation for skin in some cases. It has been known that cool feeling agents enhance a warm feeling effect when used in combination with a warm feeling agent (Patent Literature 1: U.S. Patent No. 2017/0087199A1, incorporated herein by reference in its entirety).

Meanwhile, it is reported that a warm feeling agent can increase the cool feeling effect of a specific methyl menthol derivative (Patent Literature 2: International Publication No. WO2016/153011). Even if a cool feeling agent is combined with the same type of components, the mechanism of action of an effect obtained by combining a cool feeling agent and other components is complicated, and thus the effect is unpredictable. Furthermore, the problem with a combination use of an anesthetic such as lidocaine is that cool feeling itself is lost due to the anesthetic effect. In particular, a patch prepared by stacking a gel agent on a support such as a nonwoven fabric has had the problem in that loss of cool feeling is greater than that in the case of a coating agent such as cream or lotion, and cool feeling does not last. Thus, a substance effective for maintaining cool feeling on the anesthetized skin for a long time needs to be searched.

The present inventors have conducted intensive studies to solve the above problem, and as a result, have found that vanillyl butyl ether can prolong a cool feeling effect in spite of the anesthetic effect of lidocaine.

Accordingly, the some embodiments of the present disclosure provides an external composition as follows.

[1] An external composition comprising (i) at least one selected from the group consisting of lidocaine and pharmaceutically acceptable salts thereof, (ii) a cool feeling agent, and (iii) vanillyl butyl ether.
[2] The external composition according to [1], wherein the cool feeling agent is l-menthol.
[3] The external composition according to [1] or [2], comprising 0.01 to 10% by weight of the cool feeling agent.
[4] The external composition according to any one of [1] to [3], comprising 0.005 to 1.0% by weight of vanillyl butyl ether.
[5] The external composition according to any one of [1] to [5], wherein the ratio of the cool feeling agent to vanillyl butyl ether is 1:0.001 to 1:0.4.
[6] The external composition according to any one of [1] to [5], comprising 0.1 to 10% by weight of lidocaine.
[7] The external composition according to any one of [1] to [6], comprising a gel substrate.
[8] The external composition according to [7], comprising aluminum hydroxide, sodium polyacrylate, polyacrylic acid and polyvinyl alcohol as the gel substrate.
[9] The external composition according to [7] or [8], comprising 50 to 90% by weight of water.
[10] The external composition according to any one of [1] to [9], wherein the external composition comprises lidocaine.
[11] A patch comprising a composition layer comprising the external composition according to any one of [7] to [10], the composition layer being stacked on a support.
[12] The patch according to [11], wherein the support is a nonwoven fabric.
[13] The patch according to [11] or [12], wherein the composition layer has a maximum thickness of 0.5 mm or more.

Advantageous Effect of Invention

The present disclosure provides an external composition which maintains a cool feeling effect due to a cool feeling agent such as menthol for a long time even when lidocaine which causes numbness is compounded.

DESCRIPTION OF EMBODIMENTS

Hereinafter, embodiments of the present disclosure (referred to as "the present embodiment" below) will be described in detail, but the present disclosure is not limited thereto. Various modifications may be made without departing from the gist of the present disclosure.

[External Composition]

The external composition of the present embodiment includes a cool feeling accelerator such as vanillyl butyl ether in addition to lidocaine and a cool feeling agent. Adding a cool feeling agent and a cool feeling accelerator in combination to an external composition containing lidocaine as described above suppresses a reduction of an effect of maintaining feeling of a cooling effect due to the anesthetic effect and allows a cool feeling action to be maintained for a long time. The external composition of the present embodiment can maintain a cool feeling action for a long time, e.g., 4 hours or more, even in the form of a patch with a gel agent stacked on a support. Hereinafter the external composition of the present embodiment will be described in detail.

(Form of Preparation)

The external composition of the present embodiment may be in any form of preparation as long as it is applied to the skin. Examples of forms of preparation of the external composition of the present embodiment include external pharmaceutical products for skin, such as a gel, a cream, a lotion, an emulsifier, a liquid, a patch, an aerosol, an ointment and a pack; cosmetics such as a gel, a cream, a milky lotion, a skin lotion, a lotion and a pack; and skin cleansing agents such as a body shampoo, a hair shampoo and a hair conditioner. Of these forms of preparation, preferred examples include external pharmaceutical products for skin, and more preferred examples include a gel and a patch with a gel stacked on a support.

(Lidocaine)

The external composition contains at least one selected from the group consisting of lidocaine and pharmaceutically acceptable salts thereof. The pharmaceutically acceptable salts of lidocaine may be inorganic salts or organic salts, and inorganic salts are preferred. Examples of inorganic salts include monobasic acid salts such as hydrochloride, hydrobromide and methanesulfonate; and polybasic acid salts such as fumarate, maleate, citrate and tartrate.

The amount of lidocaine and pharmaceutically acceptable salts thereof in the external composition may be determined by those skilled in the art in consideration of, for example, efficacy and skin penetration. In one aspect, the amount of lidocaine and pharmaceutically acceptable salts thereof in the external composition may be 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3.0, 4.0, 5.0, 6.0, 7.0, 8.0, 9.0, 10.0% by weight or more based on the total weight of the composition. In another aspect, the amount of lidocaine and pharmaceutically acceptable salts thereof in the external composition may be 20, 19, 18, 17, 16, 15, 14, 13, 12, 11, 10, 9, 8, 7, 6, 5, 4, 3, 2, 1% by weight or less based on the total weight of the composition. In some embodiments, the amount is, for example, preferably about 0.1 to 10% by weight, preferably about 1 to 10% by weight, and preferably about 2 to 5% by weight based on the total weight of the composition. A high concentration of lidocaine may cause precipitation of lidocaine.

The external composition may contain a local anesthetic other than lidocaine, such as dibucaine, procaine, pharmaceutical acceptable salts thereof, ethyl aminobenzoate and Thesit Destin, and an anti-inflammatory analgesic.

(Cool Feeling Agent)

A cool feeling agent may be a biocompatible, non-toxic agent having a boiling temperature of below 37° C., or 36, 35, 34, 33, 32 or 31° C. or less, or evoking cold sensation via cold receptors on the skin, including transient receptor potential melastatin 8 (TRPM8). Cool feeling agents are not particularly limited, and examples thereof include menthol, N-ethyl-p-menthane-3-carboxamide, N-(ethoxycarbonylmethyl)-3-p-menthane carboxamide, N,2,3-trimethyl-2-isopropyl butaneamide, 3-(L-methoxy)propane-1,2-diol, menthyl lactate, monomenthyl succinate, menthone glycerin acetal, 3-1-menthoxypropane-1,2-diol, menthone glycerin ether, spilanthol, monomenthyl succinate, oxalic acid menthyl ethyl amide, menthyl pyrrolidone carboxylate, and menthane carboxamide ethylpyridine. In some embodiments, the cool feeling agent includes menthol to improve a cooling effect and durability of a cool feeling effect. One of these cool feeling agents may be used alone, or two or more of them may be used in combination.

The cool feeling agent may be used in the form of a mixture. For example, menthol may be used in the form of an essential oil such as mint oil, peppermint oil and spearmint oil. The cool feeling agent also includes a pharmaceutically acceptable salt.

As used herein, "menthol" means not only I-menthol, dl-menthol and pharmaceutical acceptable salts such as menthyl lactate, but also an intermediate thereof such as isopulegol, and a mixture thereof such as oil containing I-menthol and the like, including mint oil, peppermint oil and spearmint oil. In some embodiments, the menthol includes I-menthol.

The amount of the cool feeling agent in the external composition may be determined by those skilled in the art depending on the desired level of the cool feeling effect. In one aspect, the amount of the cool feeling agent may be 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10, 11 or more % by weight based on the total weight of the composition. In another aspect, the amount of the cool feeling agent may be 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20 or less % by weight based on the total weight of the composition. The amount of I-menthol in the external composition is, for example, preferably about 0.01 to 10% by weight, preferably 0.1 to 10% by weight, preferably about 0.5 to 10% by weight, and preferably about 0.75 to 5% by weight. When the content of the cool feeling agent is 0.01% by weight of more, cool feeling effect and durability of the cool feeling effect may be improved.

In one aspect, to improve durability of the cool feeling effect, the amount of the cool feeling agent may be 6, 7, 8, 9, 10, 11, 12, 13, 14, 15, 16, 17, 18, 19, 20, 30, 40, 50, 60, 70, 80, 90, 100 or more parts by weight of lidocaine. In another aspect, the amount of the cool feeling agent may be 7, 8, 9, 10, 11, 12, 13, 14, 15, 16, 17, 18, 19, 20, 30, 40, 50, 60, 65, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500 or less parts by weight of lidocaine. In some embodiments, the amount of the cool feeling agent may be preferably about 6.25 to 500 parts by weight, preferably about 12.5 to 250 parts by weight, and more preferably about 62.5 to 100 parts by weight when calculated based on 100 parts by weight of lidocaine.

(Cool Feeling Accelerator)

As used herein, the "cool feeling accelerator" means an agent which prolongs the period of sensing a cool feeling or which increases the level of a cool feeling, when the external composition or a patch containing the same is applied to an affected part. Examples of the cool feeling accelerator include vanillyl butyl ether.

The amount of the cool feeling accelerator in the external composition may be determined by those skilled in the art depending on the desired level of the cool feeling effect. In one aspect, the content of a cool feeling accelerator may be 0.005, 0.006, 0.007, 0.008, 0.009, 0.01, 0.02, 0.03, 0.04, 0.05, 0.06, 0.07, 0.08, 0.09, 0.10, 0.11, 0.12, 0.13, 0.14, 0.15, 0.2, 0.3, 0.4, 0.5, 0.6, 0.7, 0.8, 0.9, 1, 2, 3, 4, 5, 6, 7, 8, 9, 10% by weight or more based on the total weight of the composition. In another aspect, the content of a cool feeling accelerator may be 0.006, 0.007, 0.008, 0.009, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.019, 0.20, 0.30, 0.40, 0.50, 0.60, 0.70, 0.80, 0.90, 1.00, 1.10, 1.20, 1.30, 1.40, 1.50, 2, 3, 4, 5, 6, 7, 8, 9, 10, 11, 12, 13, 14, 15% by weight or less based on the total weight of the composition. Although the amount is not intended to be limited, the content of, for example, the cool feeling accelerator, such as vanillyl butyl ether, is preferably about 0.005 to 1.0% by weight, preferably about 0.01 to 0.5% by weight, and preferably about 0.15 to 0.20% by weight based on the total weight of the composition.

The weight ratio of the cool feeling agent to the cool feeling accelerator may be in the range of about 1:0.001 to about 1:0.4 (cool feeling agent:cool feeling accelerator). In one aspect, the weight ratio of the cool feeling agent to the cool feeling accelerator may be 1:0.001, 1:0.005, 1:0.01, 1:0.05, 1:0.1, 1:0.2, 1:0.2, 1:0.3 or more. In another aspect, the weight ratio of the cool feeling agent to the cool feeling accelerator may be 1:0.005, 1:0.01, 1:0.05, 1:0.1, 1:0.2, 1:0.2, 1:0.3, 1:0.4 or less. For example, when the cool feeling agent is menthol and the cool feeling accelerator is vanillyl butyl ether, the weight ratio of menthol to vanillyl butyl ether is preferably about 1:0.002 to about 1:0.2, and preferably about 1:0.04 to about 1:0.06.

In one aspect, the amount of the cool feeling accelerator, such as vanillyl butyl ether, in the external composition may be 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 or more parts by weight of menthol. In another aspect, the amount of the cool feeling accelerator, such as vanillyl butyl ether, in the external composition may be 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40 or less parts by weight of menthol. In some embodiments, the amount of the cool feeling accelerator, such as vanillyl butyl ether, in the external composition may be preferably 0.2 to 20 parts by weight, and preferably 4 to 6 parts by weight when calculated based on 100 parts by weight of menthol.

In one aspect, the amount of the cool feeling accelerator, such as vanillyl butyl ether, in the external composition may be 0.1, 0.5, 1, 2, 3, 4, 5, 10, 15, 20, 25, 30, 35, 40, 45, 50 or more parts by weight of lidocaine. In another aspect, the amount of the cool feeling accelerator, such as vanillyl butyl ether, in the external composition may be 50, 45, 40, 35, 30, 25, 20, 15, 10, 5, 4, 3, 2, 1 or less parts by weight of lidocaine. In some embodiments, the amount of the cool feeling accelerator, such as vanillyl butyl ether, in the external composition may be preferably about 0.1 to 50 parts by weight, preferably about 0.2 to 25 parts by weight, and preferably about 0.2 to 5 parts by weight when calculated based on 100 parts by weight of lidocaine.

(Water)

The content of water is preferably about 50 to 90% by weight, more preferably about 50 to 80% by weight, and further preferably about 55 to 70% by weight based on the total amount of the external composition. When the content of water is within the above range, the cool feeling effect due to heat of vaporization tends to be improved, and durability of the cool feeling effect tends to be improved.

(Gel Substrate)

The gel substrate is not particularly limited, and for example, those which make the adhesive layer water-retainable and control flowability of the adhesive layer to maintain a predetermined shape are preferred. Using a gel substrate makes the adhesive layer being in the form of a water-containing gel which is adhesive to parts of the body.

The gel substrate is not particularly limited as long as it gives water retaining properties and/or shape retainability to the adhesive layer. Examples thereof include organic gel substrates and inorganic gel substrates. One of these gel substrates may be used alone, or two or more of them may be used in combination.

Specifically, examples of the organic gel substrates include thickening polysaccharides such as carrageenan, alginic acid, propylene glycol alginate, tara gum, locust bean gum, glucomannan, xanthan gum, welan gum, pectin, pullulan, guar gum, psyllium seed gum, welan gum, sodium alginate, mannan, gelatin, agar, casein, dextran, dextrin, soluble starch, carboxylated starch, methyl cellulose, ethyl cellulose, hydroxymethyl cellulose, hydroxyethyl cellulose, hydroxypropyl cellulose, ethyl hydroxyethyl cellulose, carboxymethyl cellulose, hydroxymethyl ethyl cellulose, methyl hydroxypropyl cellulose, hydroxypropyl cellulose phthalate, methyl cellulose, cellulose acetate, cellulose acetate and hydroxymethyl ethyl cellulose; polyacrylic acid polymers such as cross-linked polyacrylic acid, partially neutralized polyacrylic acid, polyacrylic acid-polymethacrylic acid copolymer and salts thereof (e.g., alkali metal salts such as sodium salt and potassium salt; salts of amine such as monoethanolamine, diethanolamine and triethanolamine; ammonium salts); rubber polymers such as polystyrene-polybutadiene-polystyrene copolymer, polystyrene-polyisoprene-polystyrene copolymer, polystyrene-polyethylene-polybutylene-polystyrene copolymer and polystyrene-polyethylene-polypropylene-polystyrene copolymer; and polyvinyl alcohol, carboxyvinyl polymer, urethane polymer and silicone polymer. Of these organic gel substrates, polyacrylic acid polymers and polyvinyl alcohol are preferred, and polyacrylic acid polymers are more preferred.

Of these gel substrates, organic gel substrates may exhibit excellent adhesiveness and allow the adhesive layer to be closely attached to a part of the body which needs to be cooled. In some embodiments, the gel substrate described herein includes at least an organic gel substrate.

Specifically, examples of inorganic gel substrates include double salts such as aluminum hydroxide, aluminum chloride, aluminum sulfate, aluminum nitrate, aluminum magnesium hydroxide, dihydroxyaluminum aminoacetate, kaolin and aluminum alum, and magnesium aluminometasilicate, smectite, montmorillonite, saponite, hectorite, bentonite, beidellite, nontronite, sauconite, stevensite, laponite and thickening silica. In some embodiments, the inorganic gel substrates includes aluminum hydroxide.

Of them, at least one member selected from the group consisting of aluminum hydroxide, sodium polyacrylate, polyacrylic acid and polyvinyl alcohol is preferred. Use of such a gel substrate may improve sustained release of the cool feeling agent and other components, and improve durability of a cool feeling effect and durability of a local anesthetic effect. Furthermore, controlling vaporization of water may improve durability of the cool feeling effect.

Furthermore, another preferred embodiment of the gel substrate used in the present embodiment is a combination of an organic gel substrate and an inorganic gel substrate in order to improve shape retainability. In particular, a combination of aluminum hydroxide, sodium polyacrylate, polyacrylic acid and polyvinyl alcohol is preferred because the resulting gel retains water efficiently and the effect of maintaining a cool feeling can be easily increased.

When an organic gel substrate and an inorganic gel substrate are used together as a gel substrate, their proportion is suitably determined depending on the type and the like of the organic gel substrate and the inorganic gel substrate to be used. For example, the proportion of the inorganic gel substrate is about 0.01 to 100 parts by weight, preferably about 0.1 to 30 parts by weight, and further preferably about 1 to 10 parts by weight based on 100 parts by weight of the organic gel substrate.

The content of the gel substrate may be suitably determined based on water-retaining properties, shape retainability and the type of the gel substrate to be used. In one aspect, the content of the gel substrate may be 5, 6, 7, 8, 9, 10% by weight or more based on the total amount of the adhesive layer. In another aspect, the content of the gel substrate may be 30, 31, 32, 33, 34, 35, 36, 37, 38, 39, 40, 41, 42, 43, 44, 45, 46, 47, 48, 49, 50% by weight or less based on the total amount of the adhesive layer. The content of the gel substrate is, for example, preferably 5 to 50% by weight, preferably 10 to 45% by weight, preferably 10 to 40% by weight, and preferably 10 to 35% by weight based on the total amount of the adhesive layer.

(Refreshing Agent)

The external composition of the present embodiment may also include a refreshing agent in addition to the cool feeling agent and the cool feeling accelerator to the extent that the cool feeling effect is not lost, in order to give a refreshing feeling and allow a cooling effect to be effectively felt at the site where the composition is applied.

The type of refreshing agents used in the present embodiment is not particularly limited, and examples thereof include camphor, borneol, thymol, spilanthol and methyl salicylate. One of these refreshing agents may be used alone, or two or more of them may be used in combination. Furthermore, a refreshing agent processed into particles with being adsorbed to organic or inorganic particles may also be used.

When the external composition of the present embodiment contains a refreshing agent, the content of the refreshing agent may be suitably determined depending on the level of refreshing feeling to be given and the like. In one aspect, the content of the refreshing agent may be 0, 0.01, 0.02, 0.03, 0.04, 0.05, 0.06, 0.07, 0.08, 0.09, 0.1, 0.5, 0.6, 0.7, 0.8, 0.9, 1, 2, 3, 4% by weight or more based on the external composition. In another aspect, the content of the refreshing agent may be 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5% by weight or less based on the external composition.

The content of the refreshing agent is, for example, preferably more than 0 to 10% by weight, preferably 0.001 to 10% by weight, preferably 0.01 to 5% by weight, and preferably 0.1 to 3% by weight based on the external composition.

(pH Adjuster)

The adhesive layer of the present embodiment may also include a pH adjuster. When a pH adjuster is included, the cool feeling effect and irritation can be adjusted.

The pH adjuster is not particularly limited, and examples thereof include organic acids such as tartaric acid, citric acid, lactic acid, gluconic acid, glycolic acid, malic acid, fumaric acid, methanesulfonic acid, maleic acid and acetic acid; and inorganic acids such as hydrochloric acid, phosphoric acid, sulfuric acid, nitric acid and hydrobromic acid. One of these pH adjusters may be used alone, or two or more of them may be used in combination.

The pH of the adhesive layer is preferably 4 to 7.4, preferably 4 to 7, preferably pH 4.5 to 7, and preferably 5.5 to 6.5 to improve the cooling effect. Furthermore, irritation to the skin can be suppressed.

(Other Components)

The adhesive layer may include other components as necessary in addition to the components described above. Non-limiting examples of such components include blood circulation promoters such as acidic mucopolysaccharide, chamomile, *Aesculus hippocastanum*, *Ginkgo*, *Hamamelis verginia* extract, grapefruit extract, rosemary extract, lemon extract, vitamin E and nicotinic acid derivatives; moisturizers such as glycerol, ceramide, collagen, hyaluronic acid and squalane; fatigue recovery agents such as basil extract and juniper extract; analgesics such as indomethacin, diclofenac, flurbiprofen, ketoprofen, piroxicam, felbinac, methyl salicylate and glycol salicylate; slimming agents such as tea extract, ginseng extract, caffeine, *Aesculus hippocastanum*, aminophylline, aescin, anthocyanidin, organic iodine compounds, *Hypericum erectum* extract, *Filipendula multijuga* extract, *Equisetum arvense*, *Rosmarinus officinalis*, *Hedera helix*, thiomucase and hyaluronidase; swelling reducing agents such as *Terminalia sericea*, *Ammi visnaga*, *Ammi majus*, *Aesculus hippocastanum*, anthocyanin, vitamin P, *Calendula officinalis*, concholytic acid and silanol; peeling agents such as proteases; hair-removing agents such as calcium thioglycolate; autonomic nerve-regulating agents such as γ-oryzanol; fragrances such as natural fragrances and single fragrances; antiseptics, disinfectants, antibacterial agents, colorants, moisturizers, irritation emollients, surfactants, solvents and sugar alcohols.

[Method of Production]

The external composition of the present embodiment may be produced by forming a water-containing gel by mixing the respective ingredients.

[Form]

While the external composition of the present embodiment may be directly used in the form of a water-containing gel without being supported on a supporting sheet, it is preferable that the composition be in the form of a patch in which the composition is stacked on a support from the viewpoint of easy handling such as easy attachment to the body part and easy detachment from the body part. Specific embodiments of the patch for cooling the body will be described later in the section of [Patch].

[Purposes and Method of Use]

The external composition of the present embodiment is applied to a part of the body such as the skin, which requires an action of lidocaine, e.g., a local anesthetic action, an anti-arrhythmic action, an action for preventing bronchoconstriction and an analgesic action against neuropathic pain and which needs to be cooled for a long time. More specifically, the external composition of the present embodiment may be used as a coolant for the neck, a coolant for the eye, a coolant for the face, a coolant for the leg, a coolant for the shoulder, a coolant for the lower back, a coolant for tightening of the skin, a coolant used after exercise, and a coolant for diseases with inflammation such as bruises and sprain. In particular, the external composition of the present embodiment is suitably used at an affected part which is immediately after being bruised and has heat, and needs to be cooled.

[Patch]

The patch of the present embodiment has a structure in which a composition layer made of the above external composition is stacked on a support. In the patch of the present embodiment, the surface of the external composition opposite to the side of the support is attached to the skin.

The material of the support used for supporting the external composition is not particularly limited, and may be fabric sheet such as nonwoven fabric or woven fabric, or may be a resin film.

Raw materials constituting the fabric sheet used as a support are not particularly limited. Examples thereof include synthetic fibers such as polyester including polyethylene terephthalate and polybutylene terephthalate, nylon, polypropylene, polyethylene, vinylon, rayon, acryl, acetate and polyvinyl chloride; natural fibers such as cotton, hemp, silk and paper; and a mixed fiber thereof.

In one aspect, the basis weight[what is "basis weight"?] of the nonwoven fabric is 10, 20, 30, 40, 50, 60, 70, 80, 90, 100, 110, 120, 130, 140, 10, 160, 170, 180, 190, 200, 210, 220, 230, 240, 250 g/m2 or more. In another aspect, the basis weight of the nonwoven fabric is 500, 490, 480, 470, 460, 450, 440, 430, 420, 410, 400, 390, 380, 370, 360, 350, 340, 330, 320, 310, 300, 290, 280, 270, 260, 250 g/m2 or less. In some embodiments, the basis weight of the fabric sheet used as a support is not particularly limited, and is for example, preferably 10 to 500 $g/m^2$, preferably 20 to 400 $g/m^2$, and preferably 50 to 250 $g/m^2$. The basis weight is measured as a weight of the fabric sheet cut to a basic size, for example, weight gram per $m^2$ of the fabric sheet.

Raw materials constituting the resin film used as a support are not particularly limited. Examples thereof include polyethylene, polypropylene, ethylene-vinyl acetate copolymers, polyethylene terephthalate, polyacrylonitrile, ethylene-vinyl alcohol copolymers, polyamide, polyurethane, polystyrene, polyvinyl alcohol, polyvinyl chloride, polyvinylidene chloride and polycarbonate.

The thickness of the resin film used as a support is not particularly limited, and is for example, preferably 0.01 to 10,000 μm, preferably 0.1 to 2,000 μm, and preferably 10 to 1,000 μm.

Of these supports, fabric sheet is preferred, and nonwoven fabric is more preferred because an excellent effect of maintaining a cool feeling can be obtained.

(Nonwoven Fabric)

The nonwoven fabric used as a support in the present embodiment is not particularly limited, and various known materials may be used. The fiber constituting nonwoven fabric is not particularly limited, and examples thereof include polyamide fibers; polyacrylic fibers; nylon fibers; polyolefin fibers such as polypropylene and polyethylene; polyester fibers such as polyethylene terephthalate and polybutylene terephthalate; natural fibers such as cotton, hemp, silk and paper; and a mixed fiber thereof. Of them, polyester fibers are preferred from the viewpoint of improvement and durability of a cool feeling effect.

Furthermore, in the patch of the present embodiment, the support may have a monolayer structure of a single material, or may have a multiple layer structure in which two or more of the same or different materials are stacked.

The shape of the support is not particularly limited, and may be suitably determined based on the shape of the part of the body to which the patch is attached.

In the patch of the present embodiment, while the external composition may be stacked on at least part of one side of a support, it is preferable that the external composition be provided on the entire surface of one side of a support so that the composition is closely adhered to parts of the body.

In the patch of the present embodiment, the maximum thickness of the composition layer formed on a support is not particularly limited. In one aspect, the maximum thickness H of the adhesive layer is 0.01, 0.05, 0.10, 0.20, 0.30, 0.40, 0.50, 0.55, 0.60, 0.65, 0.70, 0.75, 0.80, 0.85, 0.90, 1.00 mm or more. In another aspect, the maximum thickness H of the adhesive layer is 3.00, 2.90, 2.80, 2.70, 2.60, 2.50, 2.40, 2.30, 2.20, 2.10, 2.00, 1.95, 1.90, 1.85, 1.80, 1.75, 1.70, 1.65, 1.60, 1.55, 1.50 mm or less. In some embodiments, the maximum thickness is, for example, preferably 0.01 mm or more, preferably 0.1 mm or more, preferably 0.5 mm or more, and preferably 1 mm or more, because an excellent effect of maintaining cool feeling can be obtained. The upper limit of the maximum thickness of the external composition is not particularly limited, and is, for example, preferably 5 mm or less, preferably 3 mm or less, preferably 2 mm or less, and preferably 1.5 mm or less. The range of the thickness (maximum thickness) of the external composition is preferably 0.1 to 3 mm, preferably 0.5 to 2 mm, and preferably 1 to 1.5 mm.

The maximum thickness refers to the maximum value of the thickness of the adhesive layer from the contact surface between the nonwoven fabric and the adhesive layer when the thickness of the adhesive layer varies in the surface direction of a patch. The thickness may be measured with, for example, a caliper.

In the patch of the present embodiment, a peelable release layer may be provided as necessary on the side of the external composition, which is attached to the skin. When the patch has a release layer, the external composition can be kept hygienic until the patch is used, and handleability can be improved. The release layer is removed by peeling when the patch is used.

The material of the release layer is not particularly limited as long as it can be peeled off of the external composition. Examples thereof include resin films such as polyethylene, polyethylene terephthalate, polyacrylonitrile, an ethylene-vinyl alcohol copolymer and polypropylene; and paper which has been processed to be releasable by silicon processing and the like. When a resin film is used as the release layer, the film may also be processed to be releasable by silicon processing and the like.

The patch of the present embodiment is prepared by stacking a composition layer made of the external composition (water-containing gel) on a support. More specifically, examples of methods of preparation include a method in which the external composition is applied to a support in a predetermined thickness and a release layer is closely attached to the external composition as necessary; and a method in which the external composition is applied to a release layer in a predetermined thickness and a support is closely attached to the surface of the external composition. It is desirable that the external composition be applied to a support or a release layer in the state of a flowable gel formed as gelation due to gel substrates progresses to some extent after mixing ingredients of the external composition.

Purposes and methods of use of the patch of the present embodiment are as described in the above section of [External composition].

EXAMPLES

The present invention will be described in detail below with reference to Examples, but the present invention is not limited thereto.

Test Example

The external compositions of Examples 1 to 10 and Comparative Examples 1 to 3 were prepared so that their compositions were as described in Table 1. More specifically, the respective components of a gel substrate were gradually added to purified water and mixed. Then lidocaine, menthol, and vanillyl butyl ether (only in Examples) were added thereto to give a gel composition. The gel composition prepared as described above was applied to nonwoven fabric with a knife coater. A piece of polypropylene film, which serves as a release layer, was pressure-bonded thereto to prepare a patch.

TABLE 1

| | | Comparative Example | | | Example | | | | | | | | | |
|---|---|---|---|---|---|---|---|---|---|---|---|---|---|---|
| | | 1 | 2 | 3 | 1 | 2 | 3 | 4 | 5 | 6 | 7 | 8 | 9 | 10 |
| Local anesthetic | Lidocaine | 2 | 4 | 4 | 4 | 4 | 4 | 4 | 4 | 4 | 5 | 5 | 2 | 2 |
| Cool feeling agent | Menthol | 0.5 | 1 | 1 | 1 | 0.5 | 1 | 1 | 2.5 | 1 | 5 | 5 | 5 | 5 |
| Cool feeling accelerator | Vanillyl butyl ether | | | | 0.02 | 0.02 | 0.02 | 0.04 | 0.15 | 0.2 | 0.01 | 0.2 | 0.04 | 0.5 |
| Gel substrate | Aluminum hydroxide | 0.4 | 0.4 | 0.4 | 0.4 | 0.4 | 0.4 | 0.4 | 0.4 | 0.4 | 0.4 | 0.4 | 0.4 | 0.4 |
| | Sodium polyacrylate | 5.6 | 5.6 | 5.6 | 5.6 | 5.6 | 5.6 | 5.6 | 5.6 | 5.6 | 5.6 | 5.6 | 5.6 | 5.6 |
| | Polyacrylic acid | 1.3 | 1.3 | 1.3 | 1.3 | 1.3 | 1.3 | 1.3 | 1.3 | 1.3 | 1.3 | 1.3 | 1.3 | 1.3 |
| | Polyvinyl alcohol | 6 | 6 | 6 | 6 | 6 | 6 | 6 | 6 | 6 | 6 | 6 | 6 | 6 |
| | L-tartaric acid | 0.1 | 0.1 | 0.1 | 0.1 | 0.1 | 0.1 | 0.1 | 0.1 | 0.1 | 0.1 | 0.1 | 0.1 | 0.1 |
| | Methylparaben | 0.05 | 0.05 | 0.05 | 0.05 | 0.05 | 0.05 | 0.05 | 0.05 | 0.05 | 0.05 | 0.05 | 0.05 | 0.05 |
| | Dipropylene glycol | 7.8 | 7.8 | 7.8 | 7.8 | 7.8 | 7.8 | 7.8 | 7.8 | 7.8 | 7.8 | 7.8 | 7.8 | 7.8 |
| | Grycerol | 4 | 4 | 4 | 4 | 4 | 4 | 4 | 4 | 4 | 4 | 4 | 4 | 4 |
| | Propylparaben | 0.02 | 0.02 | 0.02 | 0.02 | 0.02 | 0.02 | 0.02 | 0.02 | 0.02 | 0.02 | 0.02 | 0.02 | 0.02 |
| | Polysorbate 80 | 1 | 1 | 1 | 1 | 1 | 1 | 1 | 1 | 1 | 1 | 1 | 1 | 1 |
| | Polyethylene glycol 40 | 3 | 3 | 3 | 3 | 3 | 3 | 3 | 3 | 3 | 3 | 3 | 3 | 3 |
| Water | Purified water | 68.2 | 65.7 | 65.7 | 65.7 | 66.2 | 65.7 | 65.7 | 64.1 | 65.5 | 60.7 | 60.5 | 63.7 | 62.2 |
| Total (% by weight) | | 100 | 100 | 100 | 100 | 100 | 100 | 100 | 100 | 100 | 100 | 100 | 100 | 100 |
| Thickness of composition layer (mm) | | 1 | 1 | 0.5 | 1 | 1 | 1 | 1 | 1 | 1 | 1 | 1 | 1 | 1 |
| Amount coated (g) | | 12 | 12 | 6 | 6 | 12 | 12 | 12 | 12 | 12 | 12 | 12 | 12 | 12 |
| Amount of menthol based on 100 parts by weight of lidocaine | | 25 | 25 | 25 | 25 | 12.5 | 25 | 25 | 62.5 | 25 | 100 | 100 | 250 | 250 |
| Amount of vanillyl butyl ether based on 100 parts by weight of menthol | | 0 | 0 | 0 | 2 | 4 | 2 | 4 | 6 | 20 | 0.2 | 4 | 0.8 | 10 |
| Cool feeling (immediately after attachment) | | A | A | A | A | A | A | A | A | A | A | A | A | A |
| Cool feeling (4 hours after attachment) | | D | D | D | C | B | B | B | A | B | B | A | B | C |

Method of Evaluation

Skin irritation of the respective patches was evaluated by 10 testers. More specifically, the patches of the respective Examples and Comparative Examples were attached to their lower back and cool feeling was evaluated. Cool feeling was evaluated based on 11 divided numerical rating scales of 0 to 10, which indicate the level of current cool feeling, with 0 being no cool feeling and 10 the maximum cool feeling assumed. The results of evaluation of the testers were averaged and rounded off to 2 decimal places. Cool feeling was evaluated based on the following evaluation criteria.

<Evaluation Criteria>
A: An average mark of 8 or more.
B: An average mark of 6 or more and less than 8
C: An average mark of 5 or more and less than 6
D: An average mark of less than 5.

The invention claimed is:

1. An external composition comprising lidocaine, a cool feeling agent, and vanillyl butyl ether, wherein
the external composition has 2% or more by weight of lidocaine,
the cool feeling agent comprises I-menthol,
the amount of I-menthol is 62.5 to 100 parts by weight based on 100 parts by weight of lidocaine,
the amount of vanillyl butyl ether is 4 to 6 parts by weight based on 100 parts by weight of I-menthol,
the composition comprises 50 to 90% by weight of water, and
the composition comprises a gel substrate.

2. The external composition according to claim 1, wherein the cool feeling agent is I-menthol.

3. The external composition according to claim 1, comprising 0.01 to 10% by weight of the cool feeling agent.

4. The external composition according to claim 1, comprising 0.005 to 1.0% by weight of vanillyl butyl ether.

5. The external composition according to claim 1, wherein the ratio of the cool feeling agent to vanillyl butyl ether is 1:0.001 to 1:0.4.

6. The external composition according to claim 1, comprising 2 to 10% by weight of lidocaine.

7. The external composition according to claim 1, comprising aluminum hydroxide, sodium polyacrylate, polyacrylic acid and polyvinyl alcohol as the gel substrate.

8. A patch comprising a composition layer comprising the external composition according to claim 1, the composition layer being stacked on a support.

9. The patch according to claim 8, wherein the support is a nonwoven fabric.

10. The patch according to claim 8, wherein the composition layer has a maximum thickness of 0.5 mm or more.

11. An external composition comprising lidocaine, a cool feeling agent, and vanillyl butyl ether, wherein
the cool feeling agent has 2.5 to 10% by weight of I-menthol,
the amount of I-menthol is 62.5 to 100 parts by weight based on 100 parts by weight of lidocaine,
the amount of vanillyl butyl ether is 4 to 6 parts by weight based on 100 parts by weight of I-menthol,
the composition comprises 50 to 90% by weight of water, and
the composition comprises a gel substrate.

12. An external composition comprising lidocaine,
a cool feeling agent,
vanillyl butyl ether,
less than 0.05% by weight methylparaben, and
less than 0.02% by weight propylparaben, wherein
the cool feeling agent comprises I-menthol,
the amount of I-menthol is 62.5 to 100 parts by weight based on 100 parts by weight of lidocaine,
the amount of vanillyl butyl ether is 4 to 6 parts by weight based on 100 parts by weight of I-menthol,
the composition comprises 50 to 90% by weight of water, and
the composition comprises a gel substrate.

13. The external composition according to claim 1, comprising 0.01 to 5% by weight of the cool feeling agent.

14. The external composition according to claim 1, comprising 0.01 to 0.5% by weight of vanillyl butyl ether.

15. The external composition according to claim 1, wherein the ratio of the cool feeling agent to vanillyl butyl ether is 1:0.001 to 1:0.2.

16. The external composition according to claim 1, wherein the ratio of the cool feeling agent to vanillyl butyl ether is 1:0.001 to 1:0.1.

17. The external composition according to claim 1, wherein the ratio of the cool feeling agent to vanillyl butyl ether is 1:0.01 to 1:0.1.

* * * * *